(12) United States Patent
Yoneda

(10) Patent No.: US 12,373,944 B2
(45) Date of Patent: Jul. 29, 2025

(54) IMAGE PROCESSING METHOD, IMAGE PROCESSING DEVICE, PROGRAM, AND RECORDING MEDIUM FOR PROCESSING MRI DATA TO DETERMINE AN AMOUNT OF TARGET MATERIAL

(71) Applicant: NATIONAL UNIVERSITY CORPORATION KUMAMOTO UNIVERSITY, Kumamoto (JP)

(72) Inventor: Tetsuya Yoneda, Kumamoto (JP)

(73) Assignee: NATIONAL UNIVERSITY CORPORATION KUMAMOTO UNIVERSITY, Kumamoto (JP)

( * ) Notice: Subject to any disclaimer, the term of this patent is extended or adjusted under 35 U.S.C. 154(b) by 406 days.

(21) Appl. No.: 17/905,501

(22) PCT Filed: Mar. 3, 2021

(86) PCT No.: PCT/JP2021/008197
§ 371 (c)(1),
(2) Date: Nov. 1, 2022

(87) PCT Pub. No.: WO2021/177353
PCT Pub. Date: Sep. 10, 2021

(65) Prior Publication Data
US 2023/0123738 A1 Apr. 20, 2023

(30) Foreign Application Priority Data
Mar. 4, 2020 (JP) .................................. 2020-037332

(51) Int. Cl.
*G06T 7/00* (2017.01)
*A61B 5/00* (2006.01)
(Continued)

(52) U.S. Cl.
CPC .......... *G06T 7/0012* (2013.01); *A61B 5/0042* (2013.01); *A61B 5/055* (2013.01);
(Continued)

(58) Field of Classification Search
CPC ......... G06T 7/0012; G06T 2207/10088; G06T 2207/30016; G06T 2207/30096;
(Continued)

(56) References Cited

U.S. PATENT DOCUMENTS 7,689,262 B2 * 3/2010 Kruger ................. G01R 33/243
324/309
8,923,591 B2 * 12/2014 Gross ............... G01R 33/56563
382/131

(Continued)

FOREIGN PATENT DOCUMENTS

JP 4982881 B2 7/2012
JP 6041356 B2 12/2016
(Continued)

OTHER PUBLICATIONS

Y. Suleimanov et al., "Magnetic resonance signal processing tool for diagnostic classification," 2016 IEEE 36th International Conference on Electronics and Nanotechnology (ELNANO), Kyiv, UKraine, 2016, pp. 175-179, doi: (Year: 2016).*

(Continued)

*Primary Examiner* — Andrae S Allison
(74) *Attorney, Agent, or Firm* — LUCAS & MERCANTI, LLP

(57) ABSTRACT

An image processing apparatus processes magnetic resonance image data acquired by scanning multiple regions of a living body. An MRI imaging apparatus scans multiple regions of the living body to acquire the magnetic resonance image data. An image processing unit generates phase difference image data from the magnetic resonance image data. A signal acquisition unit acquires a phase difference image signal from the phase difference image data. A statistic calculation unit performs statistical processing of the distribution of the phase difference image signal with respect to the phase difference for each region to calculate a statistic, for example. A target material evaluation unit evaluates the amount of the target material included in multiple regions using the statistic for each region.

11 Claims, 13 Drawing Sheets

(51) Int. Cl.
*A61B 5/055* (2006.01)
*G01R 33/56* (2006.01)

(52) U.S. Cl.
CPC .......... *A61B 5/4088* (2013.01); *A61B 5/4842* (2013.01); *G01R 33/5608* (2013.01); *G06T 2207/10088* (2013.01); *G06T 2207/30016* (2013.01); *G06T 2207/30096* (2013.01); *G06T 2207/30168* (2013.01)

(58) Field of Classification Search
CPC ........ G06T 2207/30168; A61B 5/0042; A61B 5/055; A61B 5/4088; A61B 5/4842; G01R 33/5608
See application file for complete search history.

(56) References Cited

U.S. PATENT DOCUMENTS

| | | | | |
|---|---|---|---|---|
| 12,189,008 | B1* | 1/2025 | Sun | G04F 5/14 |
| 2001/0010810 | A1* | 8/2001 | Miyoshi | G01R 33/4828 424/9.3 |
| 2004/0135577 | A1* | 7/2004 | Yatsui | G01R 33/56563 324/309 |
| 2008/0119721 | A1* | 5/2008 | Kimura | A61B 5/055 600/410 |
| 2014/0233825 | A1* | 8/2014 | Yoneda | G06T 7/0012 382/131 |
| 2017/0059682 | A1* | 3/2017 | Dagher | G01R 33/5608 |
| 2018/0203087 | A1 | 7/2018 | Ye et al. | |

FOREIGN PATENT DOCUMENTS

| | | |
|---|---|---|
| JP | 2017-184935 A | 10/2017 |
| WO | 2013047583 A1 | 4/2013 |

OTHER PUBLICATIONS

C. B. Poynton, M. Jenkinson, E. Adalsteinsson, E. V. Sullivan, A. Pfefferbaum and W. Wells III, "Quantitative Susceptibility Mapping by Inversion of a Perturbation Field Model: Correlation With Brain Iron in Normal Aging," in IEEE Transactions on Medical Imaging, vol. 34, No. 1, pp. 339-353, Jan. 2015 (Year: 2015).*

International Search Report for the corresponding application No. PCT/JP2021/008197 dated May 11, 2021, with English translation.

Cummings, et al., β-Amyloid Deposition and Other Measures of Neuropathology Predict Cognitive Status in Alzheimer's Disease, Neurobiology of Aging, vol. 17, No. 6, pp. 921-933, 1996.

Braak, et el., Frequency of Stages of Alzheimer-Related Lesions in Different Age Categories, Neurobiology of Aging, vol. 18, No. 4, pp. 351-357, 1997.

* cited by examiner

[Fig. 1]
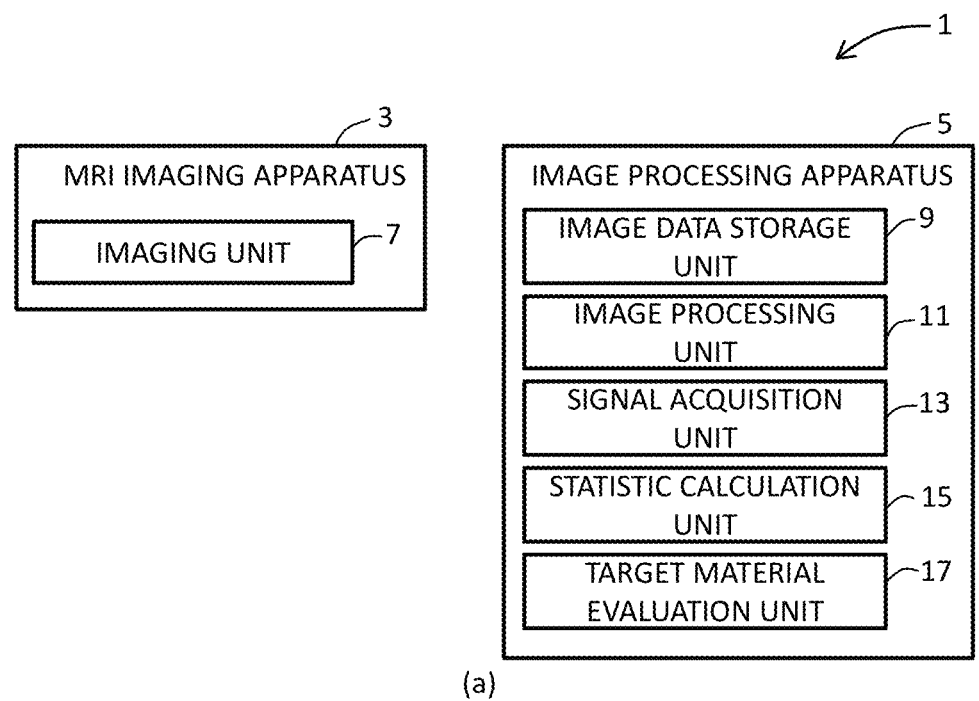
(a)
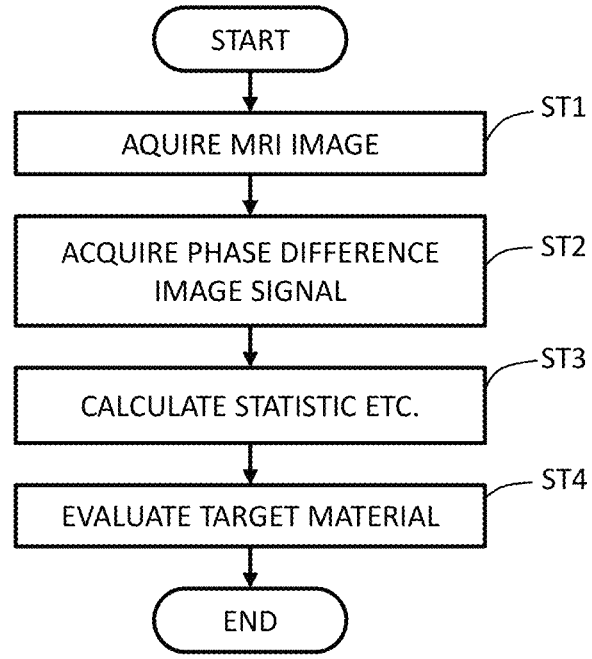
(b)

[Fig. 2]
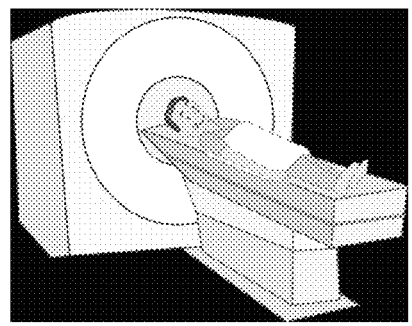
(a)
  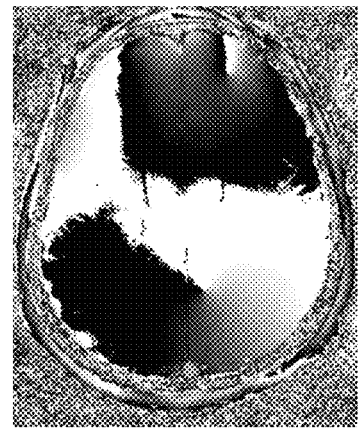
(b)          (c)          (d)
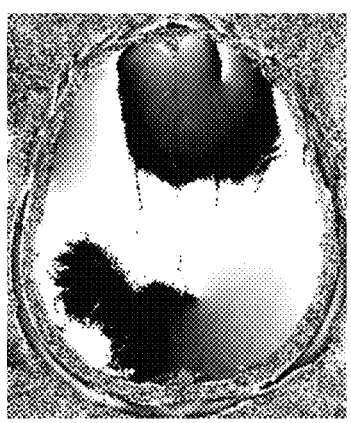 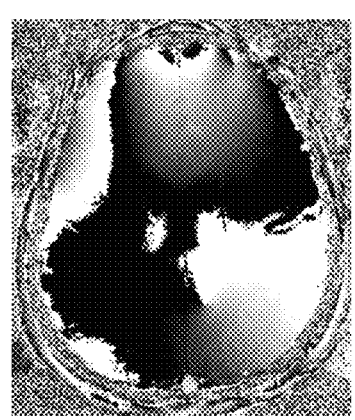 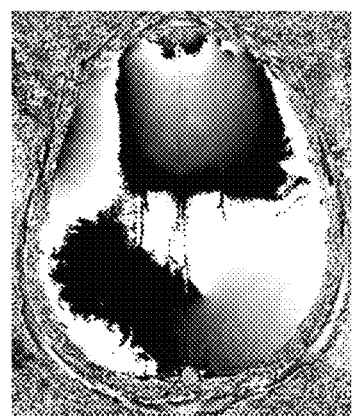
(e)          (f)          (g)

[Fig. 3]
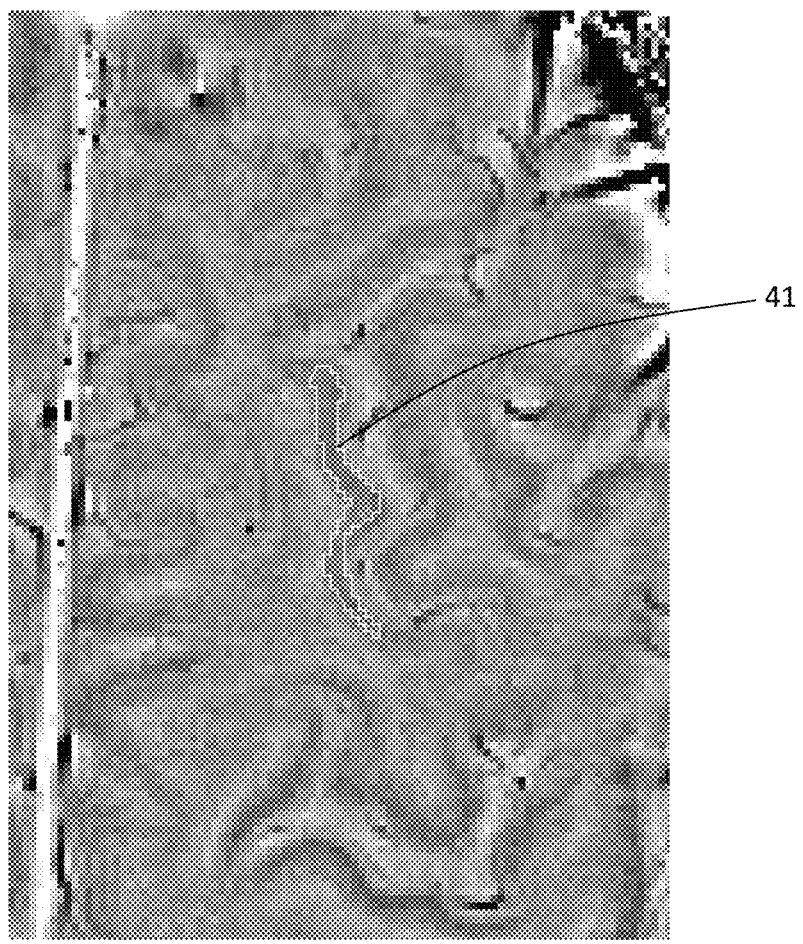

[Fig. 4]
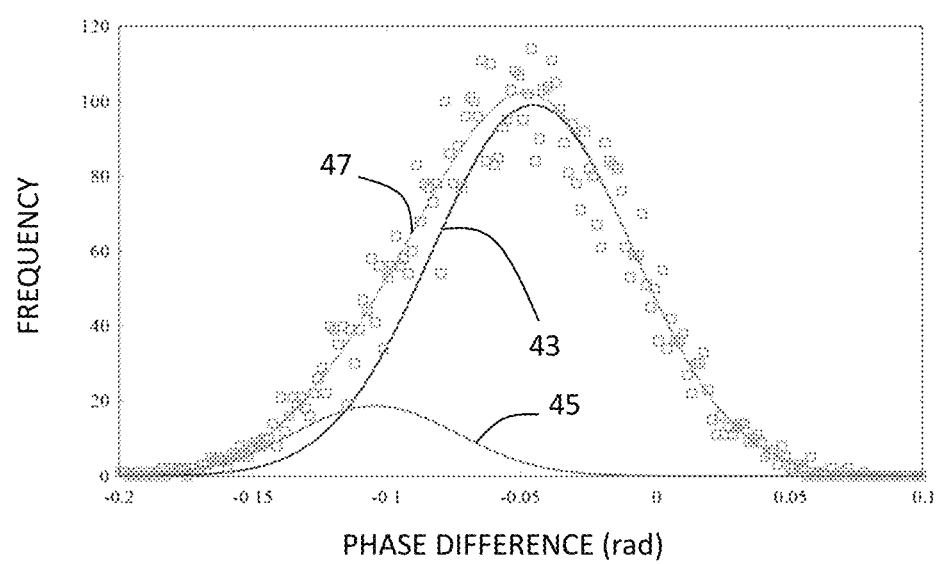

[Fig. 6]
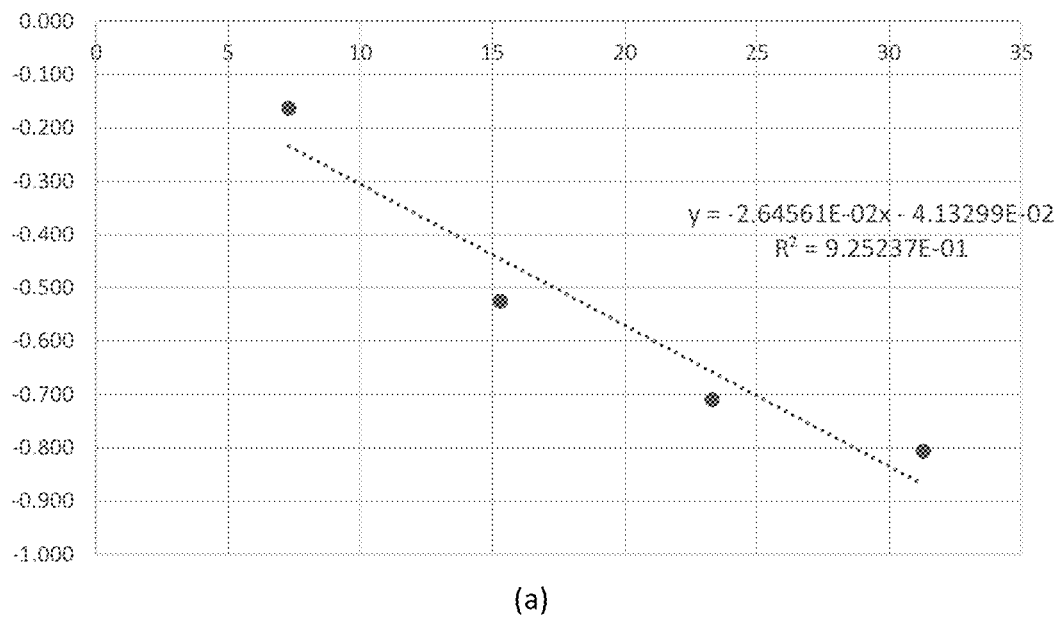
(a)
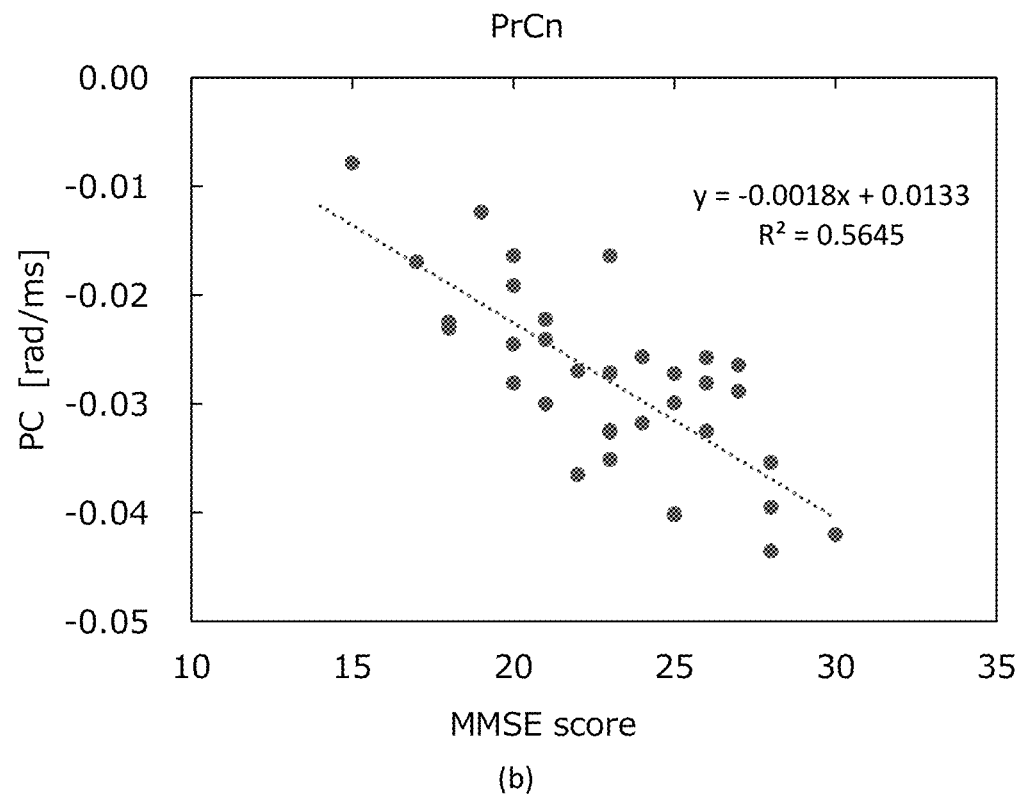
(b)

[Fig. 7]
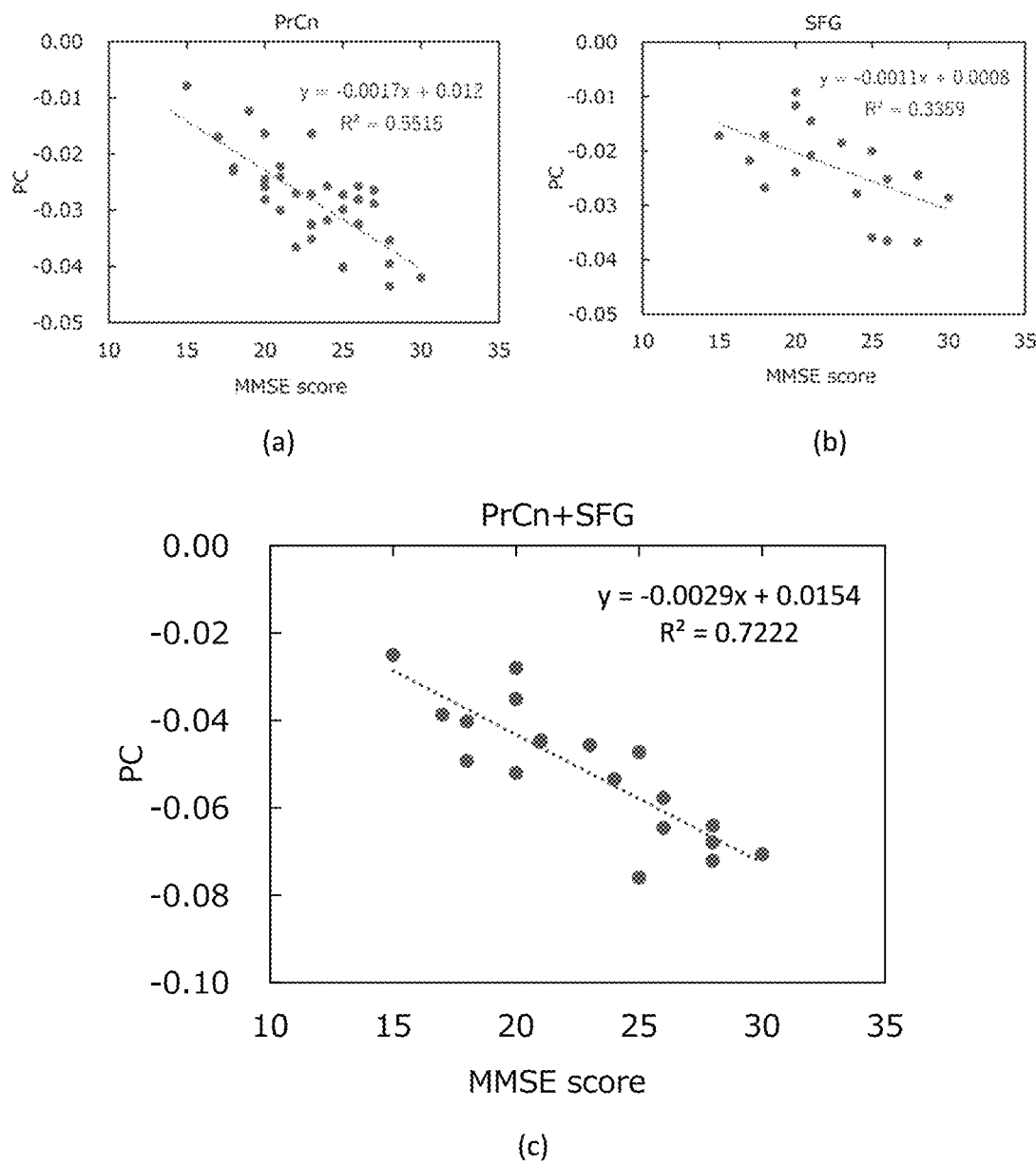

[Fig. 8]
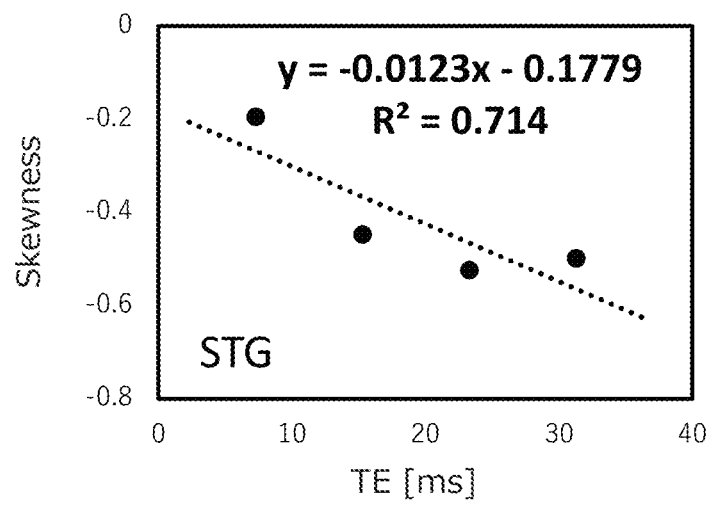
(a)
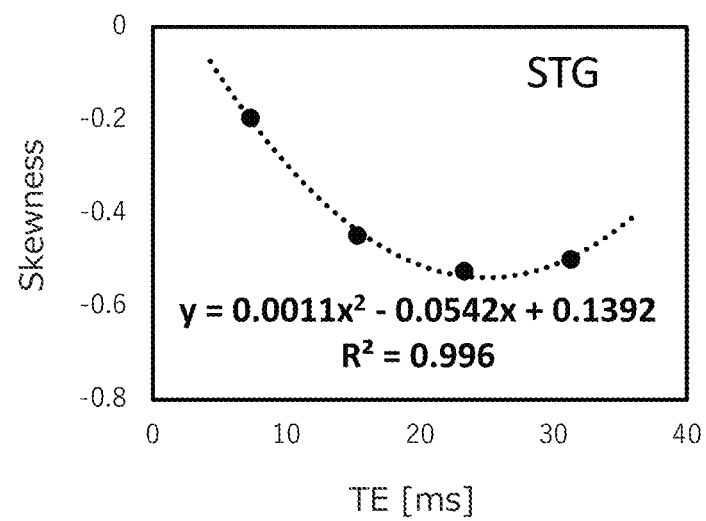
(b)

[Fig. 9]
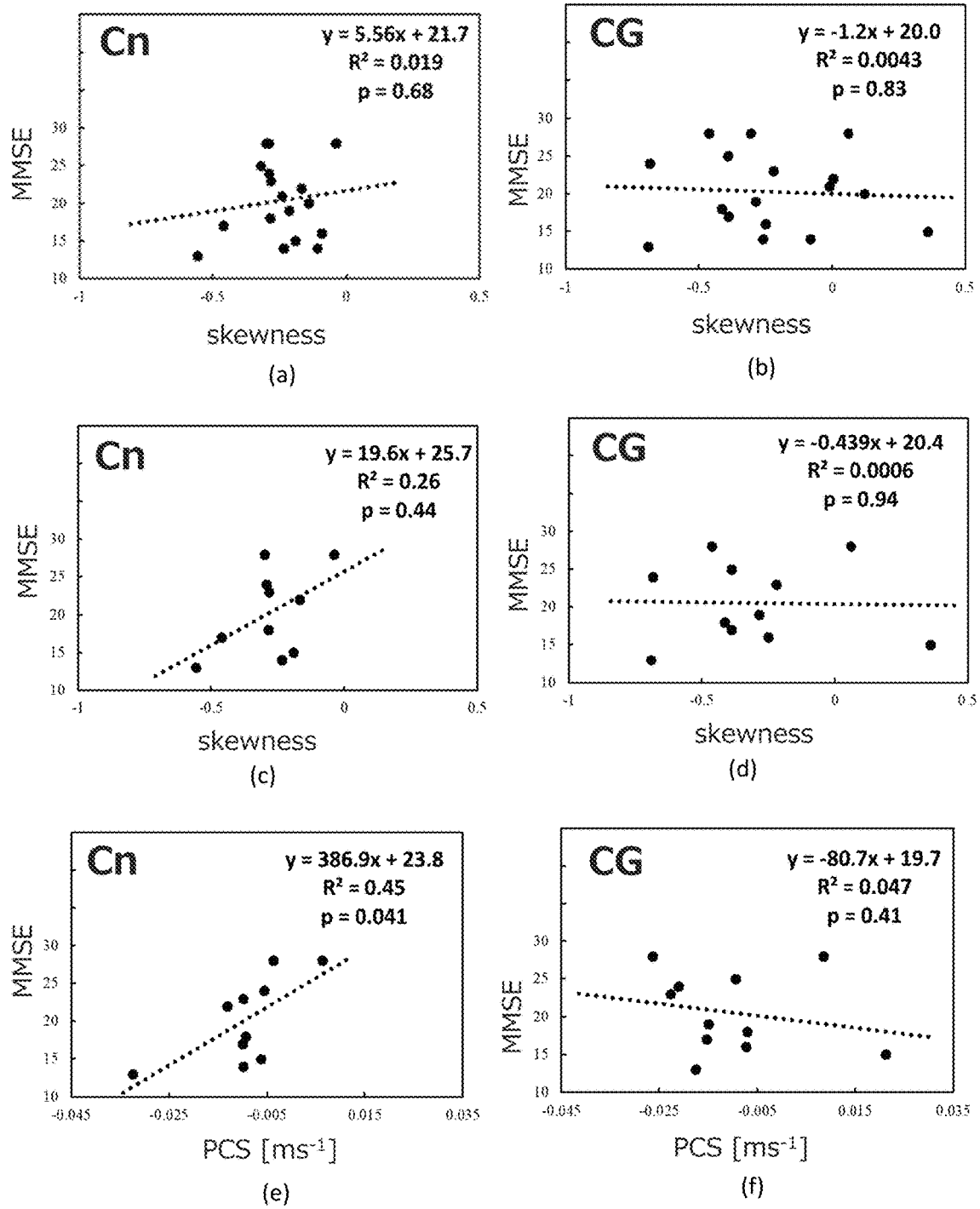

[Fig. 10]
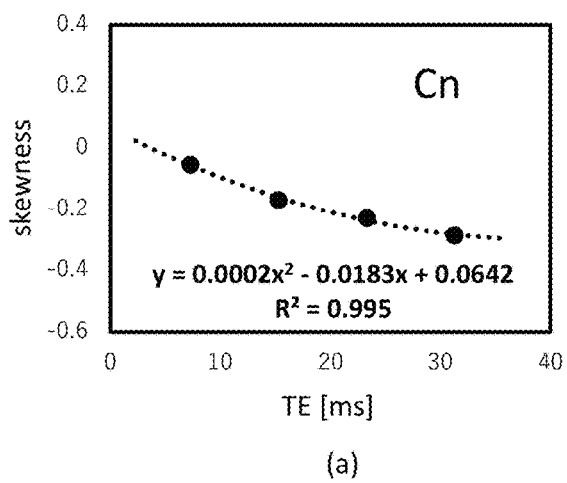
(a)
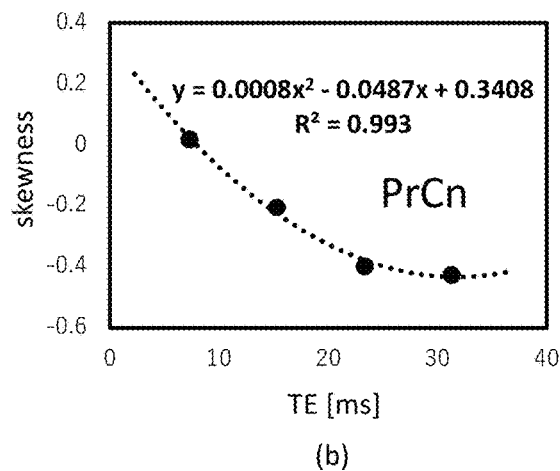
(b)
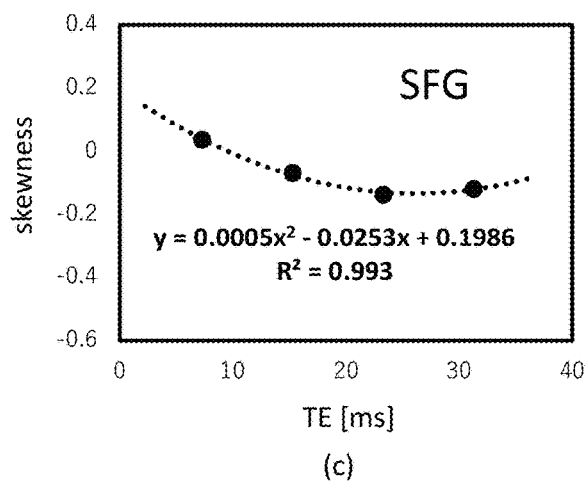
(c)
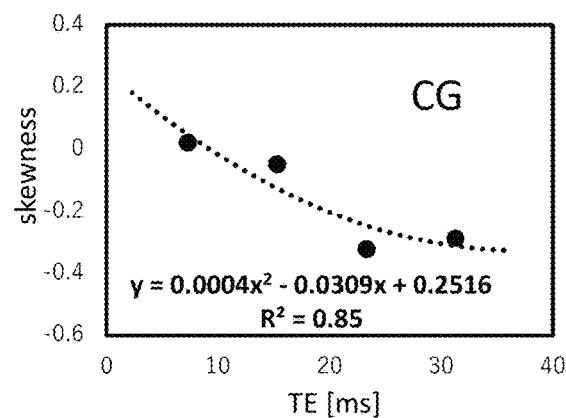
(d)

IMAGE PROCESSING METHOD, IMAGE PROCESSING DEVICE, PROGRAM, AND RECORDING MEDIUM FOR PROCESSING MRI DATA TO DETERMINE AN AMOUNT OF TARGET MATERIAL

CROSS REFERENCE TO RELATED APPLICATION

This Application is a 371 of PCT/JP2021/008197 filed on Mar. 3, 2021, which, in turn, claims priority of Japanese Patent Application No. 2020-037332 filed on Mar. 4, 2020, and the above applications are incorporated herein by reference.

TECHNICAL FIELD

The present invention relates to an image processing method, image processing apparatus, program, and recording medium, and particularly to an image processing method, etc., for performing processing of magnetic resonance image data acquired by scanning a plurality of regions of a living body.

BACKGROUND ART

For example, as described in Patent documents 1 and 2, the present inventor has been researching magnetic resonance image data obtained using the magnetic resonance imaging (MRI) method.

In Patent document 2, an arrangement is described in which the magnetic susceptibility of tissue is determined by fitting a phase difference distribution of signals of magnetic resonance acquired for a predetermined region of a living body by using multiple function groups.

CITATION LIST

Patent Literature

[Patent document 1]
 Japanese Patent No. 4,982,881
[Patent document 2]
 Japanese Patent No. 6,041,356

SUMMARY OF INVENTION

Technical Problem

However, the technique described in Patent document 2 employs nonlinear approximation. Accordingly, in some cases, it is difficult for such a technique to determine the magnetic susceptibility due to poor convergence of the nonlinear approximation, for example. On the other hand, the technique described in Patent document 1 relates to enhancement processing. That is to say, there is no description with respect to a technique for reducing the calculation burden in the analysis of image data.

Accordingly, it is a purpose of the present invention to propose an image processing method, etc., suitable for the analysis of magnetic resonance image data using simple calculation.

Solution of Problem

A first aspect of the present invention relates to an image processing method for performing processing of magnetic resonance image data acquired by scanning a plurality of regions of a living body. The image processing method includes: acquiring a signal, in which a signal acquisition unit acquires a phase difference image signal from the magnetic resonance image data; and calculating a statistic, in which a statistic calculation unit performs statistical processing of a distribution of the phase difference image signal with respect to a phase difference for each region, so as to calculate a statistic.

A second aspect of the present invention relates to the image processing method according to the first aspect. The statistical processing includes calculation of at least a part of an average, a standard deviation, kurtosis, and skewness.

A third aspect of the present invention relates to the image processing method according to the first or second aspect. The image processing method includes evaluating a target material, wherein a target material evaluation unit evaluates an amount of a target material included in multiple regions using the statistic for each region, so as to generate an evaluation result.

A fourth aspect of the present invention relates to the image processing method according to the third aspect. In the statistic calculation, the statistic calculation unit calculates a statistic evaluation value from a part of or all of the statistics for respective regions. In the target material evaluation, the target material evaluation unit evaluates an amount of the target material using the statistic evaluation value in addition to or instead of the statistic for each region.

The magnetic resonance image data can be acquired using a single-echo method or a multi-echo method. A fifth aspect of the present invention relates to the image processing method according to the third or fourth aspect. In a case in which the magnetic resonance image data is acquired using a multi-echo method, in the statistic calculation, the statistic calculation unit calculates the statistic using statistical processing performed for multiple echo times.

In the target material evaluation, the target material evaluation unit evaluates an amount of the target material using a change in an echo time. In the statistic calculation, in a case in which accumulation of the target material that is higher than a detection limit occurs in a given region, the statistic calculation unit calculates the statistic for the given region based on an approximation model using data for which a determination coefficient, which represents a degree of reproduction of the statistic from the echo time based on an approximation model between the echo time and the statistic, is larger than a cut-off value, and/or calculates the statistic by performing approximation processing based on a higher-order model than a linear function for multiple values obtained by statistical processing.

A sixth aspect of the present invention relates to the image processing method according to any one of the third aspect through fifth aspect. The target material in each region increases or decreases due to factors that differ from aging of the living body in addition to the factor of aging. The statistic increases or decreases due to an increase or decrease of the target material due to at least a factor that differs from aging. In the target material evaluation, the target material evaluation unit evaluates an amount of the target material that increases or decreases due to a factor that differs from aging.

A seventh aspect of the present invention relates to the image processing method according to the sixth aspect. The target material is iron bound to a protein. Multiple regions of the living body include multiple regions in the brain. The iron bound to a protein in each region increases due to a factor that differs from aging of the living body in addition to the factor of aging.

An eighth aspect of the present invention relates to the image processing method according to the sixth or seventh aspect. The target material in each region has a predetermined order of increasing or decreasing due to a factor that differs from aging. In the target material evaluation, the target material evaluation unit evaluates an amount of the target material that increases or decreases due to a factor that differs from aging using the order.

A ninth aspect of the present invention relates to an image processing apparatus configured to perform processing of magnetic resonance image data acquired by scanning a plurality of regions of a living body. The image processing apparatus includes: a signal acquisition unit configured to acquire a phase difference image signal from the magnetic resonance image data; and a statistic calculation unit configured to perform statistical processing of a distribution of the phase difference image signal with respect to a phase difference for each region, so as to calculate a statistic.

A tenth aspect of the present invention relates to the image processing apparatus according to the ninth aspect. The statistical processing includes calculation of at least a part of an average, a standard deviation, kurtosis, and skewness.

An eleventh aspect of the present invention relates to the image processing apparatus according to the ninth or tenth aspect. The image processing apparatus further includes a target material evaluation unit configured to evaluate an amount of a target material included in multiple regions using the statistic for each region, so as to generate an evaluation result.

A twelfth aspect of the present invention relates to the image processing apparatus according to the eleventh aspect. The statistic calculation unit calculates a statistic evaluation value from a part of or all of the statistics for respective regions. The target material evaluation unit evaluates an amount of the target material using the statistic evaluation value in addition to or instead of the statistic for each region.

The magnetic resonance image data can be acquired using a single-echo method or a multi-echo method. A thirteenth aspect of the present invention relates to the image processing apparatus according to the eleventh or twelfth aspect. In a case in which the magnetic resonance image data is acquired using a multi-echo method, the statistic calculation unit calculates the statistic using statistical processing performed for multiple echo times. The target material evaluation unit evaluates an amount of the target material using a change in an echo time. In a case in which accumulation of the target material that is higher than a detection limit occurs in a given region, the statistic calculation unit calculates the statistic for the given region based on an approximation model using data for which a determination coefficient, which represents a degree of reproduction of the statistic from the echo time based on an approximation model between the echo time and the statistic, is larger than a cut-off value, and/or calculates the statistic by performing approximation processing based on a higher-order model than a linear function for multiple values obtained by statistical processing.

A fourteenth aspect of the present invention relates to the image processing apparatus according to any one of the eleventh aspect through the thirteenth aspect. The target material in each region increases or decreases due to factors that differ from aging of the living body in addition to the factor of aging. The statistic increases or decreases due to an increase or decrease of the target material due to at least a factor that differs from aging. The target material evaluation unit evaluates an amount of the target material that increases or decreases due to a factor that differs from aging.

A fifteenth aspect of the present invention relates to the image processing apparatus according to the fourteenth aspect. The target material is iron bound to a protein. Multiple regions of the living body include multiple regions in the brain. The iron bound to a protein in each region increases due to a factor that differs from aging of the living body in addition to the factor of aging.

A sixteenth aspect of the present invention relates to the image processing apparatus according to the fourteenth or fifteenth aspect. The target material in each region has a predetermined order of increasing or decreasing due to a factor that differs from aging. The target material evaluation unit evaluates an amount of the target material that increases or decreases due to a factor that differs from aging using the order.

A seventeenth aspect of the present invention relates to a program configured to instruct a computer to function as the image processing apparatus according to any one of the ninth aspect through the sixteenth aspect.

An eighteenth aspect of the present invention relates a computer-readable recording medium configured to record the program according to the seventeenth aspect.

It should be noted that, with each aspect according to the present invention, the image processing unit may extract the phase difference using the magnetic resonance image data so as to generate the phase difference image data. Also, the signal acquisition unit may acquire the phase difference image signal from the phase difference image data. Also, the image processing apparatus may be provided with an image processing unit.

Advantageous Effects of Invention

With each aspect according to the present invention, the magnetic resonance image data is analyzed using simple calculation, i.e., statistical processing. Accordingly, this provides analysis in a simple manner without complicated calculations such as nonlinear approximation, for example.

BRIEF DESCRIPTION OF DRAWINGS

FIG. 1A is a block diagram showing an example configuration of an image processing system 1 according to an embodiment of the present invention, and FIG. 1B is a flowchart showing an example of processing.

FIG. 2 is a diagram for explaining an MRI imaging apparatus 3 shown in FIG. 1A.

FIG. 3 shows an example of a region of interest 41 set in phase difference image data.

FIG. 4 shows an example of a histogram generated by a statistic calculation unit 15 shown in FIG. 1A using a single-echo method.

FIG. 6A is a diagram showing the rate of change of the statistic with respect to the echo time acquired as shown in FIGS. 5A-5D, and FIG. 6B is a diagram showing that the rate of change has a high correlation with an evaluation index.

FIGS. 7A and 7B each show the rate of change of the statistic for each region, and FIG. 7C is a diagram showing the sum thereof.

FIG. 8A is a diagram showing a case using a linear model as a model that is assumed to be used for each region, and FIG. 8B is a diagram showing a case using a quadratic function model as a model that is assumed to be used for each region.

FIG. 9 is a diagram for explaining the improvement of accuracy when the cut-off is applied for the Cn and CG.

FIG. 10 is a diagram showing fit results for the Cn, PrCn, SFG, and CG when a quadratic function model is used.

DESCRIPTION OF EMBODIMENTS

Figure 5A:
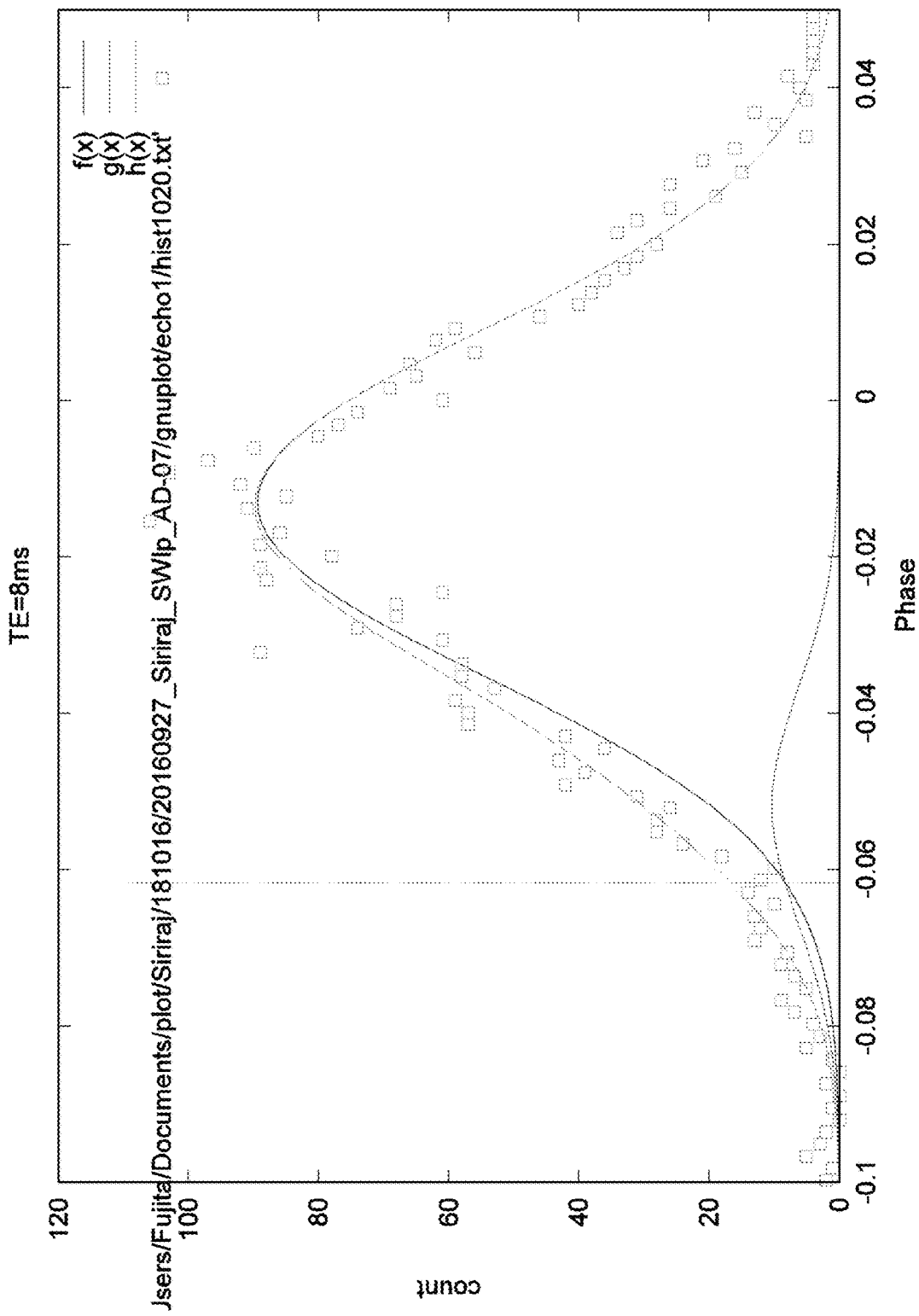
FIGS. 5A-5D show an example of the histogram generated by the statistic calculation unit 15 shown in FIG. 1A using a multi-echo method.

Description will be made below with reference to drawings regarding examples of the present invention. It should be noted that the present is not restricted to such examples.

Examples

FIG. 1A is a block diagram showing an example of an image processing system 1 according to an embodiment of the present invention. FIG. 1B is a flowchart showing an example of processing.

Description will be made with reference to FIG. 1A regarding an example configuration of the image processing system 1. The image processing system 1 includes an MRI imaging apparatus 3 and an image processing apparatus 5.

The MRI imaging apparatus 3 includes an imaging unit 7.

The image processing apparatus 5 includes an image data storage unit 9, an image processing unit 11, a signal acquisition unit 13 (an example of a "signal acquisition unit" in the present claims), a statistic calculation unit 15 (an example of a "statistic calculation unit" in the present claims), and a target material evaluation unit 17 (an example of a "target material evaluation unit" in the present claims).

It should be noted that the present invention may be provided as an arrangement in which the MRI imaging apparatus 3 includes a part of or all of the components included in the image processing apparatus.

Description will be made with reference to FIG. 1B regarding an example of the operation of the image processing system 1 shown in FIG. 1A.

With the MRI imaging apparatus 3, the imaging unit 7 scans a human body, and acquires captured image data (Step ST1). In this step, the imaging unit 7 may preferably produce an image using an scanning method (e.g., gradient echo method) typically provided by the MRI imaging apparatus 3. Also, the captured image data may be acquired using a single-echo method (collection method using a single echo) or a multi-echo method (collection method using multiple echoes).

The image processing apparatus 5 is capable of communicating with the MRI imaging apparatus 3. The MRI imaging apparatus 3 transmits the captured image data (an example of "magnetic resonance image data" in the present claims) produced by the imaging unit 7 to the image processing apparatus 5. The image data storage unit 9 of the image processing apparatus 5 stores the captured image data thus received.

The image processing unit 11 generates phase difference image data based on the captured image data stored by the image data storage unit 9 using a technique described in Patent document 2, for example.

The signal acquisition unit 13 sets a region of interest (ROI) in the phase difference image data, and acquires phase difference image signals in the region of interest (Step ST2). For example, the signal acquisition unit 13 may analyze the phase difference image data so as to automatically set the region of interest. Also, the image processing apparatus 5 may display the phase difference image data so as to allow the region of interest to be set according to an instruction by the user.

The statistic calculation unit 15 generates a histogram of the phase difference image signals thus acquired with the horizontal axis as the phase difference and with the vertical axis as its frequency. Furthermore, the statistic calculation unit 15 calculates the statistic using statistical processing for each region included in the region of interest (Step ST3). Examples of statistical processing include calculation of the average, standard deviation, kurtosis, skewness, etc. The statistic is a value obtained by calculation using statistical processing.

The target material evaluation unit 17 evaluates the amount of a target material using the statistic calculated by the statistic calculation unit 15 so as to generate an evaluation result (Step ST4).

The target material is, for example, iron bound to a protein. The main pathological factors that cause Alzheimer's disease (which will be referred to as "AD" hereafter) include the accumulation of amyloid beta in the brain. In many cases, accumulation of amyloid beta occurs in the cerebral cortex (cerebral neocortex), leading to the formation of amyloid senile plaque (which will be referred to as "AP" hereafter). AP generates a neurotoxin, leading to the occurrence of damage in cranial nerves in the interior of the cerebral cortex. It is considered that, as a result, this damages brain functions, leading to the occurrence of dementia. The iron accumulated in AP is reflected in the phase difference image signal acquired from the magnetic resonance image data acquired by capturing images of AP.

As explained later, the present inventor has found that there is a correlation between a clinical index such as the Mini-Mental State Examination (MMSE) or the like and the statistic calculated by statistical processing of the phase difference image signal. The target material evaluation unit 17 is capable of evaluating the accumulation (amount) of iron in AP using the statistic based on the phase difference image signal distribution extracted from the magnetic resonance image data obtained by scanning the cerebral cortex, so as to provide information having a correlation with a clinical index (e.g., the MMSE or the like, which is a typical cognitive function index for AD or dementia). The target material evaluation unit 17 may be configured to calculate a clinical index as an evaluation result, for example. Also, the target material evaluation unit 17 may be configured to provide a physician or the like with reference information to be used in the interpretation of the clinical index.

Furthermore, in a case of employing a multi-echo method, there is a strong correlation between changes in the echo time and the clinical index. Accordingly, in a case of employing such a multi-echo method, in Step ST3, the statistic calculation unit 15 may calculate the statistic for each echo, so as to calculate the rate of change in the statistic with respect to changes in the echo time, for example. In Step ST4, the target material evaluation unit 17 may evaluate the amount of the target material based on the rate of change in the statistic with respect to changes in the echo time. In this step, the target material evaluation unit 17 may evaluate the amount of the target material using the statistic, a statistic evaluation value, etc.

Furthermore, it has been found that there is a correlation between the clinical index and the statistic evaluation value of the statistic for each region (evaluation value obtained by calculation using a part of or all of the statistics for multiple regions, examples of which include the sum of the statistics calculated for the respective regions) (see FIG. 7). Accordingly, in Step ST3, the statistic calculation unit 15 may calculate the statistic for each region. In addition, the statistic calculation unit 15 may calculate the statistic evaluation value. In Step ST4, the target material evaluation unit 17 may evaluate the amount of the target material using the statistic evaluation value in addition to or instead of the statistic acquired for each region. Also, in a case of employing the multi-echo method, the amount of the target material may be evaluated using the rate of change of the statistic with respect to changes in echo time, the evaluation value of the rate of change of the statistic calculated using a part of or all of the rates of change of the statistic for the respective regions, or the like, for example.

Description will be made regarding the reason why a statistic (in particular, skewness) has a correlation with the amount of AP accumulation. In the brain, iron that binds to proteins includes iron that increases with aging and iron that accumulates in AP. With the phase difference as the horizontal axis and with its frequency as the vertical axis, in a normal state, i.e., in a situation in which there is no iron in AP, the histogram usually has a predetermined distribution (e.g., single Gaussian distribution). There is a difference in the center axis, for example, between the distribution of iron that accumulates in AP and the distribution of iron that increases with aging. Accordingly, the histogram of iron that increases with aging and iron that accumulates in AP is different from the predetermined distribution of iron that increases with aging (see FIG. 4). Because of the difference in the distribution, there is a difference in a statistic (e.g., skewness or the like) calculated by statistical processing between a case in which there is a large amount of iron in AP and a case in which there is a small amount of iron in AP. Furthermore, it is known that there is a correlation (a linear correlation or the like) between AP accumulation and clinical indexes (e.g., see Cummings et al., β-AMYLOID DEPOSITION AND OTHER MEASURES OF NEUROPATHOLOGY PREDICT COGNITIVE STATUS IN ALZHEIMER'S DISEASE, Neurobiology of Aging, Vol. 17, No. 6, pp. 921-933, 1996, or the like). Accordingly, the statistic has a correlation with the amount of iron in AP, and has a correlation with clinical indexes.

It should be noted that there is a known method for detecting iron in the brain using Quantitative Susceptibility Mapping (QSM). However, this method provides evaluation based on both iron due to aging and amyloid iron without distinction. Accordingly, such a method has a disadvantage in that it is incapable of providing correct evaluation with respect to AP. As a result, the evaluation has no correlation with clinical indexes. In contrast, in the present method, iron in AP is correctly evaluated using the fact that the amyloid-derived distortion in the histogram can be detected using a statistic (in particular, skewness). Accordingly, AP evaluation has a correlation with clinical indexes. In particular, with the present technique, the magnetic susceptibility of the amyloid (iron included in the amyloid) is evaluated although it is not identified by QSM.

Furthermore, it is known that the areas of AP accumulation in the brain become wider over time (see Braak et al., Frequency of Stages of Alzheimer-Related Lesions in Different Age Categories, Neurobiology of Aging, Vol. 18, No. 4, pp. 351-357, 1997, or the like). Because the area of AP accumulation becomes wider over time in the brain, it becomes possible to organically evaluate the progress of AD (preclinical stage or mild dementia stage) by separately evaluating brain regions (brain function areas) classified based on differences in accumulation at a given time point. Such a difference in accumulation can be assumed to have effects on cognitive function. Accordingly, relative evaluation between brain regions may provide a more effective index of the correlation with cognitive dysfunction. After the onset of AD, as differences become smaller between brain regions, accumulation advances in substantially all regions. Accordingly, it is considered that, with the present technique, the results advance in a direction in which the differences between regions disappear.

FIG. 2 is a diagram for explaining the MRI imaging apparatus 3 shown in FIG. 1A. FIG. 2A is a diagram for explaining an imaging situation. FIGS. 2B through 2G are diagrams each showing an example of magnetic resonance image data.

As shown in FIG. 2A, a test subject is entered into a cylinder of the MRI imaging apparatus 3. The MRI imaging apparatus 3 is capable of acquiring images of internal information with respect to the test subject based on Nuclear Magnetic Resonance (NMR) by using a magnetic field applied to the cylinder. The image data produced by scanning with the MRI imaging apparatus 3 is a complex image of rotating magnetization vectors each having a magnitude and an angle. Typically, the MRI imaging apparatus 3 is capable of using magnitude image data and phase image data (see Patent document 2). Here, the magnitude image is an image of the magnitude components of magnetic resonance signals. The phase image is an image of the rotational angles of the magnetization vectors (see FIGS. 2B through 2G). The image data storage unit 9 stores the magnitude image data and the phase image data.

The image processing unit 11 generates phase difference image data based on the magnitude image data and the phase image data (see FIG. 3). The phase difference image data can be generated using a technique described in Patent document 2 (see the explanation with respect to the generation of phase difference images, for example).

For the sake of caution, description will be made regarding the generation of the phase difference image data. If the MRI signal is acquired using a long TE (echo time), this leads to the occurrence of phase wrapping in the phase image. That is to say, if the actual phase has a phase value that is larger than 2π, the phase value recorded in the phase image has a phase value obtained by subtracting 2πn (n represents an integer) from the actual phase. Accordingly, this leads to the occurrence of a striped pattern in the phase image, resulting in a problem in that the phase image cannot represent the original phase values. The image processing unit 11 removes this phase wrapping and extracts each phase difference using techniques such as those described in Patent document 2, thereby generating the phase difference image data.

The signal acquisition unit 13 sets a region of interest (ROI) in the phase difference image data. FIG. 3 shows an example of a region of interest 41 set in the phase difference image data. The signal acquisition unit 13 may display the phase difference image data on a display unit such as a display or the like of the image processing apparatus 5, for example. Also, an arrangement may be made to allow the user of the image processing apparatus 5 to set the region of interest using an input unit such as a mouse or the like. Also, the region of interest may be automatically determined and set by learning or the like. The region of interest may be defined as a two-dimensional region or a three-dimensional region.

The signal acquisition unit 13 acquires phase difference data in each ROI (an example of a "phase difference image signal" in the present claims) of the MRI signals acquired from the tissue included in the region of interest.

The statistic calculation unit 15 divides the phase difference data in each ROI of the MRI signals for each region so as to generate the phase difference distribution. For example, the statistic calculation unit 15 generates a histogram with the horizontal axis as the phase difference and the vertical axis as its frequency. Subsequently, the statistic is calculated for each region. Examples of such a statistic include an average, a standard deviation, kurtosis, skewness, etc., of the phase difference distribution for each region.

FIG. 4 shows an example of the histogram generated by the statistic calculation unit 15. The horizontal axis represents the phase difference (rad), and the vertical axis represents its frequency (number of items of data). The line 43 represents the iron distribution due to aging of a living body (aging iron phase distribution). The line 45 represents the distribution of amyloid iron (amyloid iron distribution). If there is no amyloid iron distribution, the distribution is a single Gaussian distribution as represented by the line 43. The existence of an amyloid iron distribution causes a difference from the Gaussian distribution as represented by the line 47. The statistic calculated based on the line 47 reflects the change from the line 43. For example, skewness is an index that represents the asymmetry of the distribution. The amyloid iron distribution is plotted on the left side in FIG. 4 with respect to the central axis of the aging iron phase distribution (line 43). Accordingly, the line 47 has an asymmetric shape as transformed from the shape of the line 43. Accordingly, by calculating skewness for the line 47, such an arrangement is capable of evaluating the amyloid iron distribution. Similarly, the amyloid iron distribution leads to a change in the kurtosis of the distribution.

Accordingly, by calculating the kurtosis of the line 47, this is capable of evaluating the amyloid iron distribution (line 45). Furthermore, the inventor has confirmed that the amyloid iron distribution (line 45) can also be evaluated based on the average value, standard deviation, or the like of the line 47.

Figure 5B:
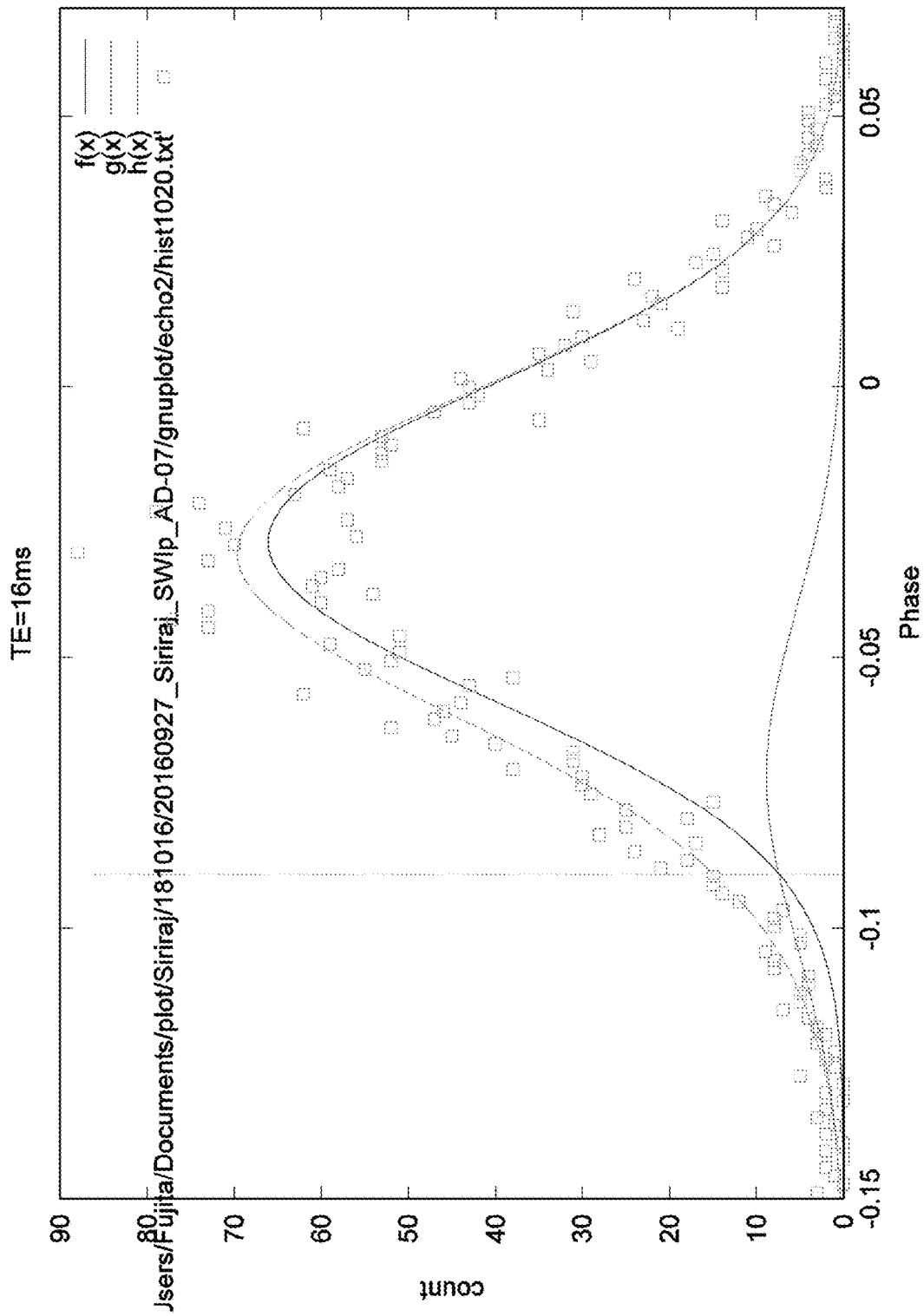
Figure 5C:
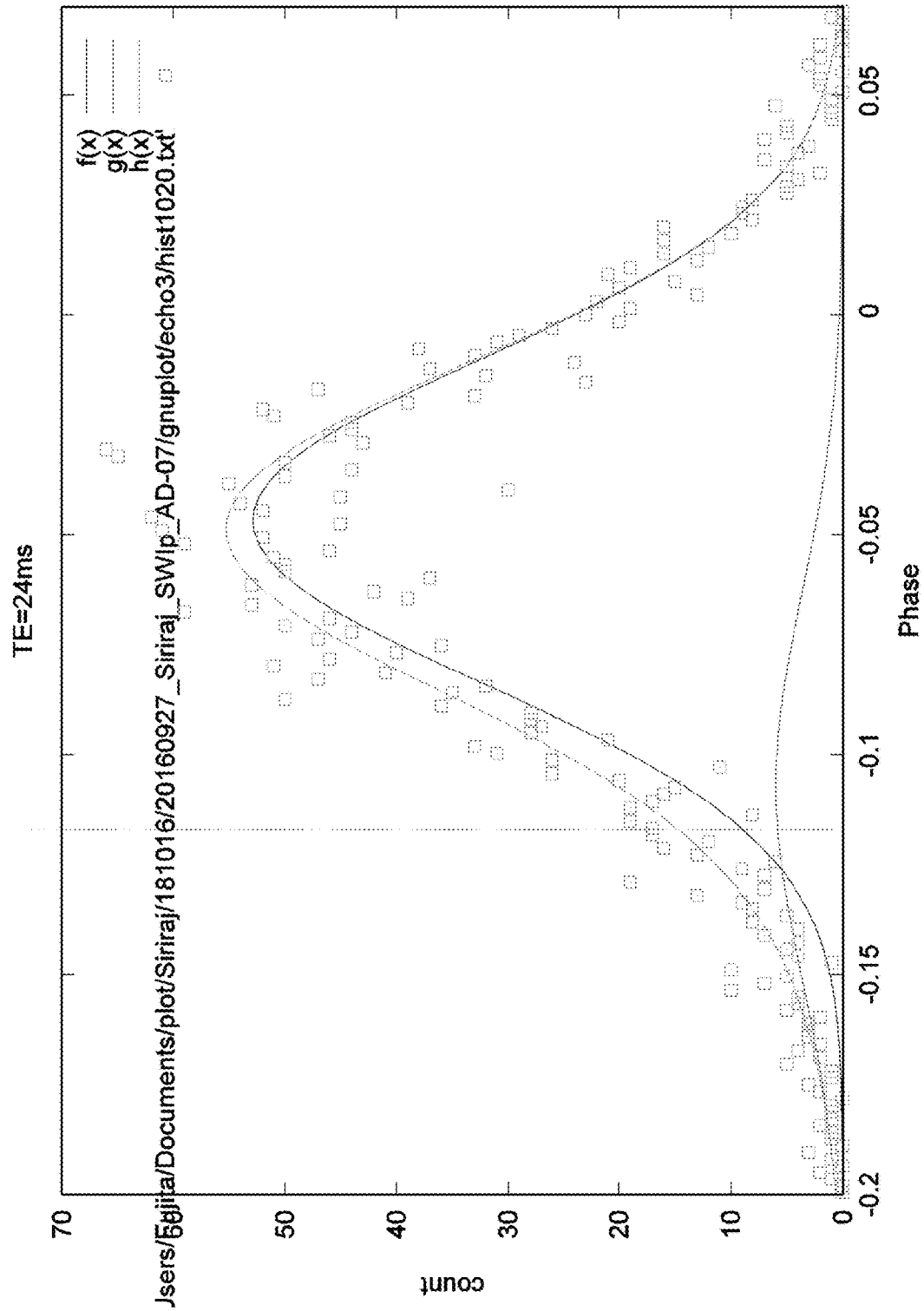
Figure 5D:
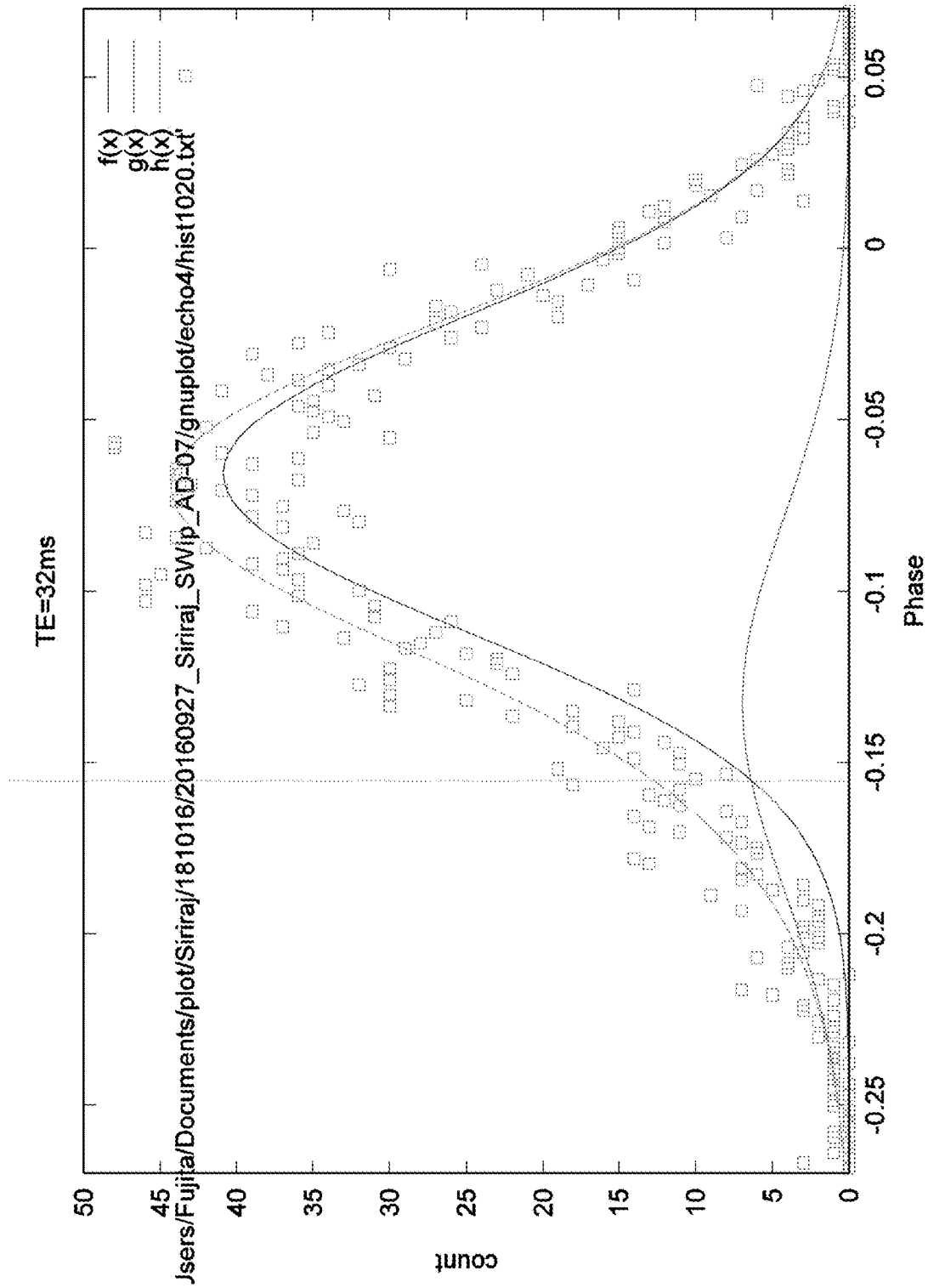

FIG. 5 shows examples of the phase difference image signal distribution acquired using a multi-echo method. In FIG. 5, the echo time increases in the order of FIG. 5A, FIG. 5B, FIG. 5C, and FIG. 5D. As the echo time increases, the amyloid iron distribution shifts significantly in the negative direction. Accordingly, the amyloid iron distribution has an effect on the statistic calculated for each echo.

FIG. 6A shows the rate of change (slope) of the skewness calculated for each graph in FIG. 5 with respect to the TE (echo time) of each echo. Based on FIG. 6A, this allows the amyloid iron distribution to be evaluated with the rate of change as a quantitative value.

FIG. 6B is a graph obtained by plotting data for 39 patients with the horizontal axis as the MMSE score and with the vertical axis as the rate of change obtained in the same manner as shown in FIG. 6A. The values shown in FIG. 6A have a high correlation with the MMSE score. Accordingly, it is anticipated that the rate of change thus obtained in the same manner as shown in FIG. 6A can be used as a reference by a physician or the like to determine the MMSE score. Furthermore, it is anticipated that there is also the potential to automatically determine the MMSE score. The rate of change obtained in the same manner as shown in FIG. 6A is an example of an "evaluation result" in the present invention.

FIG. 7 shows an example of evaluation based on the statistic evaluation value. FIGS. 7A and 7B each show the rate of change of the statistic (skewness) for each region. FIG. 7A shows an example of the precuneus (PrCn), and FIG. 7B shows an example of the superior frontal gyrus (SFG). FIG. 7C shows a graph obtained by plotting the sum of the skewness of the two regions described above for each individual (an example of a "statistic evaluation value" in the present claims). As shown in FIG. 7C, it has been found that the sum of the skewness of the two regions has a higher correlation with the MMSE. It should be noted that after the onset of AD, it can be considered that the results will advance in a direction in which the difference between the regions disappears. Accordingly, instead of the sum, a calculation value such as the difference between the regions or the like may be employed as the statistic evaluation value, for example.

In the same manner, the present inventor has confirmed that the statistics (average, standard deviation, skewness, kurtosis) acquired using the single-echo method have a correlation with clinical indexes (the MMSE score or the like). Furthermore, the present inventor has confirmed that the statistic acquired using the single-echo method and the rate of change acquired using the multi-echo method each have a correlation with clinical indexes.

The target material evaluation unit 17 evaluates the amount of amyloid iron for each region using the fact that the statistic, statistic evaluation value, etc., calculated for each region by the statistic calculation unit 15 reflect the amyloid iron distribution for each region.

It should be noted that, with the present invention, if a given material is reflected in the phase difference image signal, such an arrangement is capable of evaluating the amount of the given material as a target material based on the statistic of the phase difference image signal.

Also, the present invention can be introduced as a non-invasive examination method.

Description will be made with reference to FIGS. 8 through 10 regarding an improved technique for acquiring skewness using multiple TEs (echo times).

With the random variable as X, skewness, which is a basic statistic, is represented as a third-order moment as represented by Equation (1) using the average $\mu$ ($\mu$<0) of X. Here, E(x) represents an expected value of x, and $\sigma$ represents the standard deviation of the random variable. By expanding the expected value in the numerator in Equation (1), Equation (2) is derived. X represents the phase value for each echo time (TE). Accordingly, with the gyromagnetic ratio as y, and with the local magnetic field as B, X is represented by Equation (3). As can be understood from Equation (2), skewness is represented by a third-order polynomial of TE.

X is on the order of 0.1 [rad]. Accordingly, skewness can be approximated based on the lowest-order approximation with respect to TE using Equation (3), i.e., using a linear approximation with respect to TE as represented by Equation (4). Accordingly, under this approximation, it can be assumed that there is a linear relation between skewness and TE. Referring to FIG. 8A, for a short TE, it can be assumed that the linear model represented by Equation (4) can be employed. Here, "skewness" represents skewness, k represents the proportional coeffect of skewness (PCS), i.e., a parameter relating to the average magnetic susceptibility of amyloid iron), and $k_0$ represents a constant. As compared with Equation (3), it can be assumed that the proportional constant k includes a factor affected by the magnetic susceptibility.

However, in some cases, the data does not exhibit stable linearity due to data variation. As a result, this leads to a tendency to reduce the correlation with the MMSE. In order to solve such a problem, a determination coefficient $R^2$ was calculated so as to represent how well skewness can be reproduced when TE is determined if the relation between skewness and TE is approximated by the linear model represented by Equation (4). $R^2$ is a value ranging from 0 to 1. When $R^2$ is 0, this represents a case in which skewness cannot be reproduced at all. As the $R^2$ value becomes larger, the accuracy of reproduction becomes higher. When $R^2$ is 1, this represents a case in which skewness can be perfectly reproduced. For example, $R^2$ can be acquired as follows. That is to say, a ROI set for the brain of a subject to be tested is applied to phase images generated using different TEs, and the data points of skewness for the respective TEs are plotted with TE as the horizontal axis and with skewness as the vertical axis, so as to acquire $R^2$. A cut-off is set for the determination coefficient $R^2$, and only data points that provide fit accuracy higher than a predetermined level are selected. FIG. 9 shows an example of the cut-off. In this example, the average value of $R^2$ acquired for each brain region is set as the cut-off. Furthermore, only data that exhibits $R^2$ higher than the cut-off is employed as reliable data. By applying an approximation model with the reliable data, such an arrangement is able to provide skewness with high precision.

Also, when the average value p becomes somewhat larger, the minimum approximation as represented by Equation (4) may no longer hold true. Referring to FIG. 8B, it can be considered that, in some cases, evaluation cannot be made using sufficiently short TEs such as 30 ms, 40 ms, and so forth. In order to solve such a problem, as shown in FIG. 8B, the approximation order is raised, and evaluation is made based on a modified model using a quadratic function represented by Equation (5). Here, "skewness" represents skewness, and $k_2$, $k_1$, and $k_0$ are constants. As shown in FIG. 8B, this dramatically raises the fit accuracy. As described above, in a case in which the data includes data points that 100719960) cannot be used for evaluation with sufficiently short TEs, it can be considered that, by employing a higher-accuracy polynomial expression without omitting higher-order terms (second-order and third-order), this is capable of raising the approximation accuracy.

Specific description will be made with reference to FIG. 9 regarding the usage of the cut-off. Description will be made regarding the improvement of accuracy using the cut-off with the Cn and CG. FIGS. 9A and 9B respectively show the correlation between skewness and the MMSE with respect to the Cn and CG in a case in which the cut-off is not used. In this case, $R^2$ was 0.019 and 0.0043 for the Cn and CG, respectively.

FIGS. 9C and 9E respectively show the correlation between skewness and the MMSE and the correlation between the PCS and the MMSE with respect to the Cn in a case in which the cut-off is used. For the Cn, with such an arrangement using the cut-off, the $R^2$ value was 0.26 for the result shown in FIG. 9C, and 0.45 for the result shown in FIG. 9E. It can be recognized that this dramatically raises the $R^2$ value, i.e., this dramatically raises the linearity. FIGS. 9D and 9F respectively show the correlation between skewness and the MMSE and the correlation between the PCS and the MMSE with respect to the CG in a case in which the cut-off is used. For the CG, with such an arrangement using the cut-off, the $R^2$ value was 0.047 for the result shown in FIG. 9F, which is a dramatic increase. However, the $R^2$ value was 0.0006, which is a small value, for the result shown in FIG. 9D. That is to say, the linearity was not improved. It can be considered that the amyloid accumulation in the CG is small. As described above, it has been found that such an arrangement has a detection limit. Accordingly, with such an arrangement in which the cut-off is applied using the $R^2$ value for a region in which amyloid accumulation is equal to or larger than the detection limit, it can be anticipated that such an arrangement provides improved linearity.

Specific description will be made with reference to FIG. 10 regarding the usage of the quadratic function model. FIGS. 10A, 10B, 10C, and 10D show the fit results for the Cn, PrCn, SFG, and CG, respectively. With such an arrangement in which such a quadratic function model is used, the $R^2$ values are 0.995, 0.993, 0.993, and 0.85. That is to say, such an arrangement dramatically improves the fit accuracy. With this, such an arrangement has the potential to improve prediction accuracy. It should be noted that a higher-order function model that is higher than the quadratic function model may be used. Also, when the relation between skewness and TE is approximated using a model, the cut-off may be applied using a determination coefficient $R^2$ that represents whether skewness can be reproduced from TE.

[Equation 1]

$$\frac{E(X-\mu)^3}{\sigma^3} \quad (1)$$

$$E(X^3) - 3\mu E(X^2) + 3\mu^2 E(X) - \mu^3 \quad (2)$$

$$X = -\gamma BTE \quad (3)$$

$$\text{skewness} \simeq k \cdot TE + k_0 \quad (4)$$

$$\text{skewness} \simeq k_2 \cdot TE^2 + k_1 \cdot TE + k_0 \quad (5)$$

REFERENCE SIGNS LIST 1 image processing system, 3 MRI imaging apparatus, 5 image processing apparatus, 7 imaging unit, 9 image data storage unit, 11 image processing unit, 13 signal acquisition unit, 15 statistic calculation unit, 17 target material evaluation unit.

The invention claimed is:

1. An image processing method for performing processing of magnetic resonance image data acquired by scanning a plurality of regions of a living body, the image processing method comprising:
  acquiring signal, in which a signal acquisition unit acquires a phase difference image signal from the magnetic resonance image data;
  calculating a statistic, in which a statistic calculation unit performs statistical processing of a distribution of the phase difference image signal with respect to a phase difference for each region, so as to calculate the statistic; and
  evaluating a target material, wherein a target material evaluation unit evaluates an amount of the target material included in the plurality of regions using the statistic for the each region, so as to generate an evaluation result,
  wherein, in a case in which the magnetic resonance image data is acquired using a multi-echo method, in the statistic calculation, the statistic calculation unit calculates the statistic using the statistical processing performed for a plurality of echo times,
  wherein, in the target material evaluation, the target material evaluation unit evaluates the amount of the target material using a change in an echo time, and wherein, in the statistic calculation, in a case in which accumulation of the target material that is higher than a detection limit occurs in a given region, the statistic is calculated for the given region based on an approximation model using data for which a determination coefficient, which represents a degree of reproduction of the statistic from the echo time based on the approximation model between the echo time and the statistic, is larger than a cut-off value, and/or the statistic is calculated by performing approximation processing based on a higher-order model than a linear function for the plurality of values obtained by the statistical processing.

2. The image processing method according to claim 1, wherein the statistical processing includes calculation of at least a part of an average, a standard deviation, kurtosis, and skewness.

3. The image processing method according to claim 1, wherein the target material in the each region increases or decreases due to factors that differ from aging of the living body in addition to the factor of aging,
   wherein the statistic increases or decreases due to an increase or decrease of the target material due to at least a factor that differs from aging,
   and wherein, in the target material evaluation, the target material evaluation unit evaluates the amount of the target material that increases or decreases due to the factor that differs from aging.

4. The image processing method according to claim 3, wherein the target material is iron bound to a protein,
   wherein the plurality of regions of the living body includes a plurality of regions in a brain,
   and wherein the iron bound to the protein in the each region increases due to the factor that differs from aging of the living body in addition to the factor of aging.

5. The image processing method according to claim 3, wherein the target material in the each region has a predetermined order of increasing or decreasing due to the factor that differs from aging,
   and wherein, in the target material evaluation, the target material evaluation unit evaluates the amount of the target material that increases or decreases due to the factor that differs from aging using the order.

6. An image processing apparatus configured to perform processing of magnetic resonance image data acquired by scanning a plurality of regions of a living body, the image processing apparatus comprising:
   a signal acquisition unit configured to acquire a phase difference image signal from the magnetic resonance image data;
   a statistic calculation unit configured to perform statistical processing of a distribution of the phase difference image signal with respect to a phase difference for each region, so as to calculate a statistic; and
   a target material evaluation unit configured to evaluate an amount of a target material included in the plurality of regions using the statistic for the each region, so as to generate an evaluation result,
   wherein, in a case in which the magnetic resonance image data is acquired using a multi-echo method, the statistic calculation unit calculates the statistic using the statistical processing performed for a plurality of echo times,
   wherein the target material evaluation unit evaluates the amount of the target material using a change in an echo time, and
   wherein, in a case in which accumulation of the target material that is higher than a detection limit occurs in a given region, the statistic calculation unit calculates the statistic for the given region based on an approximation model using data for which a determination coefficient, which represents a degree of reproduction of the statistic from the echo time based on the approximation model between the echo time and the statistic, is larger than a cut-off value, and/or calculates the statistic by performing approximation processing based on a higher-order model than a linear function for the plurality of values obtained by the statistical processing.

7. The image processing apparatus according to claim 6, wherein the statistical processing includes calculation of at least a part of an average, a standard deviation, kurtosis, and skewness.

8. The image processing apparatus according to claim 6, wherein the target material in the each region increases or decreases due to factors that differ from aging of the living body in addition to the factor of aging,
   wherein the statistic increases or decreases due to an increase or decrease of the target material due to at least a factor that differs from aging,
   and wherein the target material evaluation unit evaluates the amount of the target material that increases or decreases due to the factor that differs from aging.

9. The image processing apparatus according to claim 8, wherein the target material is iron bound to a protein,
   wherein the plurality of regions of the living body includes a plurality of regions in a brain,
   and wherein the iron bound to the protein in the each region increases due to the factor that differs from aging of the living body in addition to the factor of aging.

10. The image processing apparatus according to claim 8, wherein the target material in the each region has a predetermined order of increasing or decreasing due to the factor that differs from aging,
    and wherein the target material evaluation unit evaluates the amount of the target material that increases or decreases due to the factor that differs from aging using the order.

11. A non-transitory computer-readable recording medium configured to record a computer program configured to instruct a computer to function as the image processing apparatus according to claim 6.

* * * * *